(12) United States Patent
Blum et al.

(10) Patent No.: US 7,404,636 B2
(45) Date of Patent: Jul. 29, 2008

(54) ELECTRO-ACTIVE SPECTACLE EMPLOYING MODAL LIQUID CRYSTAL LENSES

(75) Inventors: Ronald D. Blum, Roanoke, VA (US); William Kokonaski, Gig Harbor, WA (US); Dwight P. Duston, Laguna Niguel, CA (US)

(73) Assignee: E-Vision, LLC, Roanoke, VA (US)

( * ) Notice: Subject to any disclaimer, the term of this patent is extended or adjusted under 35 U.S.C. 154(b) by 10 days.

(21) Appl. No.: 11/036,501

(22) Filed: Jan. 14, 2005

(65) Prior Publication Data
US 2005/0185135 A1 Aug. 25, 2005

Related U.S. Application Data

(63) Continuation-in-part of application No. 10/644,112, filed on Aug. 20, 2003, and a continuation-in-part of application No. 10/422,128, filed on Apr. 24, 2003, now Pat. No. 6,857,741, which is a continuation-in-part of application No. 10/387,143, filed on Mar. 12, 2003, now Pat. No. 7,023,594, which is a continuation-in-part of application No. 10/281,204, filed on Oct. 28, 2002, now Pat. No. 6,733,130, and a continuation-in-part of application No. 10/046,244, filed on Jan. 16, 2002, now Pat. No. 6,871,951.

(60) Provisional application No. 60/142,053, filed on Jul. 2, 1999, provisional application No. 60/143,626, filed on Jul. 14, 1999, provisional application No. 60/147,813, filed on Aug. 10, 1999, provisional application No. 60/150,545, filed on Aug. 25, 1999, provisional application No. 60/150,564, filed on Aug. 25, 1999, provisional application No. 60/161,363, filed on Oct. 26, 1999, provisional application No. 60/536,238, filed on Jan. 14, 2004, provisional application No. 60/404,657, filed on Aug. 20, 2002, provisional application No. 60/375,028, filed on Apr. 25, 2002, provisional application No. 60/363,549, filed on Mar. 13, 2002, provisional application No. 60/401,700, filed on Aug. 7, 2002, provisional application No. 60/261,805, filed on Jan. 17, 2001, provisional application No. 60/331,419, filed on Nov. 15, 2001, provisional application No. 60/326,991, filed on Oct. 5, 2001.

(51) Int. Cl.
*G02C 7/02* (2006.01)

(52) U.S. Cl. ......................................... 351/159; 351/41

(58) Field of Classification Search ................. 351/159, 351/41
See application file for complete search history.

(56) References Cited

U.S. PATENT DOCUMENTS

| | | |
|---|---|---|
| 2,437,642 A | 3/1948 | Henroleau |
| 2,576,581 A | 11/1951 | Edwards |
| 3,161,718 A | 12/1964 | de Luca |
| 3,245,315 A | 4/1966 | Marks et al. |
| 3,309,162 A | 3/1967 | Kosanke et al. |
| 3,614,215 A | 10/1971 | Mackta |
| 3,738,734 A | 6/1973 | Tait et al. |
| 3,791,719 A | 2/1974 | Kratzer et al. |
| 4,174,156 A | 11/1979 | Glorieux |
| 4,181,408 A | 1/1980 | Senders |
| 4,190,330 A | 2/1980 | Berreman |
| 4,264,154 A | 4/1981 | Petersen |
| 4,279,474 A | 7/1981 | Belgorod |
| 4,300,818 A | 11/1981 | Schachar |
| 4,320,939 A | 3/1982 | Mueller |
| 4,373,218 A | 2/1983 | Schachar |
| 4,395,736 A | 7/1983 | Fraleux |
| 4,418,990 A | 12/1983 | Gerber |
| 4,423,929 A | 1/1984 | Gomi |
| 4,457,585 A | 7/1984 | DuCorday |
| 4,466,703 A | 8/1984 | Nishimoto |
| 4,466,706 A | 8/1984 | Lamothe, II |
| 4,529,268 A | 7/1985 | Brown |
| 4,564,267 A | 1/1986 | Nishimoto |
| 4,572,616 A | 2/1986 | Kowel et al. |
| 4,577,928 A | 3/1986 | Brown |
| 4,601,545 A | 7/1986 | Kern |
| 4,609,824 A | 9/1986 | Munier et al. |
| 4,712,870 A | 12/1987 | Robinson et al. |

| | | | | | | |
|---|---|---|---|---|---|---|
| 4,756,605 A | 7/1988 | Okada et al. | | RE35,691 E | 12/1997 | Theirl et al. |
| 4,772,094 A | 9/1988 | Sheiman | | 5,712,721 A | 1/1998 | Large |
| D298,250 S | 10/1988 | Kildall | | 5,728,155 A | 3/1998 | Anello et al. |
| 4,787,733 A | 11/1988 | Silva | | 5,739,959 A | 4/1998 | Quaglia |
| 4,787,903 A | 11/1988 | Grendahl | | 5,777,719 A | 7/1998 | Williams et al. |
| 4,795,248 A | 1/1989 | Okada et al. | | 5,815,233 A | 9/1998 | Morokawa et al. |
| 4,813,777 A | 3/1989 | Rainville et al. | | 5,815,239 A | 9/1998 | Chapman et al. |
| 4,818,095 A | 4/1989 | Takeuchi | | 5,861,936 A | 1/1999 | Sorenson |
| 4,836,652 A | 6/1989 | Oishi et al. | | 5,877,876 A | 3/1999 | Birdwell |
| 4,842,400 A * | 6/1989 | Klein ......................... 351/158 | | 5,900,720 A | 5/1999 | Kallman et al. |
| 4,880,300 A | 11/1989 | Payner et al. | | 5,949,521 A | 9/1999 | Williams et al. |
| 4,890,903 A | 1/1990 | Treisman et al. | | 5,953,098 A | 9/1999 | Lieberman et al. |
| 4,904,063 A | 2/1990 | Okada et al. | | 5,956,183 A | 9/1999 | Epstein et al. |
| 4,907,860 A | 3/1990 | Noble | | 5,963,300 A | 10/1999 | Horwitz |
| 4,909,626 A | 3/1990 | Purvis et al. | | 5,971,540 A | 10/1999 | Ofner |
| 4,919,520 A | 4/1990 | Okada et al. | | 5,980,037 A | 11/1999 | Conway |
| 4,921,728 A | 5/1990 | Takiguchi et al. | | 5,999,328 A | 12/1999 | Kurtin et al. |
| 4,927,241 A | 5/1990 | Kuijk | | 6,040,947 A | 3/2000 | Kurtin et al. |
| 4,929,865 A | 5/1990 | Blum | | 6,050,687 A | 4/2000 | Bille et al. |
| 4,930,884 A | 6/1990 | Tichenor et al. | | 6,069,742 A | 5/2000 | Silver |
| 4,944,584 A | 7/1990 | Maeda et al. | | 6,086,204 A | 7/2000 | Magnante |
| 4,945,242 A | 7/1990 | Berger et al. | | 6,095,651 A | 8/2000 | Williams et al. |
| 4,952,788 A | 8/1990 | Berger et al. | | 6,099,117 A | 8/2000 | Gregory |
| 4,958,907 A | 9/1990 | Davis | | 6,115,177 A | 9/2000 | Vossler |
| 4,961,639 A | 10/1990 | Lazarus | | 6,145,987 A | 11/2000 | Baude et al. |
| 4,968,127 A | 11/1990 | Russell et al. | | 6,188,525 B1 | 2/2001 | Silver |
| 4,981,342 A | 1/1991 | Fiala | | 6,191,881 B1 | 2/2001 | Tajima |
| 4,991,951 A | 2/1991 | Mizuno et al. | | 6,213,602 B1 | 4/2001 | Smarto |
| 5,015,086 A | 5/1991 | Okaue et al. | | 6,270,220 B1 | 8/2001 | Keren |
| 5,030,882 A | 7/1991 | Solero | | 6,271,915 B1 | 8/2001 | Frey et al. |
| 5,050,981 A | 9/1991 | Roffman | | 6,305,802 B1 | 10/2001 | Roffman et al. |
| 5,066,301 A | 11/1991 | Wiley | | 6,325,508 B1 | 12/2001 | Decreton et al. |
| 5,067,795 A | 11/1991 | Senatore | | 6,350,031 B1 | 2/2002 | Lashkari et al. |
| 5,073,021 A | 12/1991 | Marron | | 6,396,622 B1 | 5/2002 | Alden |
| 5,076,665 A | 12/1991 | Petersen | | 6,437,762 B1 | 8/2002 | Birdwell |
| 5,089,023 A | 2/1992 | Swanson | | 6,437,925 B1 | 8/2002 | Nishioka |
| 5,091,801 A | 2/1992 | Ebstein | | 6,464,363 B1 | 10/2002 | Nishioka et al. |
| 5,108,169 A | 4/1992 | Mandell | | 6,491,394 B1 | 12/2002 | Blum et al. |
| 5,114,628 A | 5/1992 | Hofer et al. | | 6,501,443 B1 | 12/2002 | McMahon |
| 5,130,856 A | 7/1992 | Tichenor et al. | | 6,554,425 B1 | 4/2003 | Roffman et al. |
| 5,142,411 A | 8/1992 | Fiala | | 6,609,794 B2 | 8/2003 | Levine |
| 5,150,234 A | 9/1992 | Takahashi et al. | | 6,614,408 B1 | 9/2003 | Mann |
| 5,171,266 A | 12/1992 | Wiley et al. | | 6,616,275 B1 | 9/2003 | Dick et al. |
| 5,182,585 A | 1/1993 | Stoner | | 6,616,279 B1 | 9/2003 | Davis et al. |
| 5,184,156 A * | 2/1993 | Black et al. .................. 351/158 | | 6,618,208 B1 | 9/2003 | Silver |
| 5,200,859 A | 4/1993 | Payner et al. | | 6,626,532 B1 | 9/2003 | Nishioka et al. |
| 5,208,688 A | 5/1993 | Fergason et al. | | 6,631,001 B2 | 10/2003 | Kuiseko |
| 5,229,797 A | 7/1993 | Futhey et al. | | 6,682,195 B2 | 1/2004 | Dreher |
| 5,229,885 A | 7/1993 | Quaglia | | 6,709,108 B2 | 3/2004 | Levine et al. |
| 5,231,430 A | 7/1993 | Kohayakawa | | 6,738,199 B2 | 5/2004 | Nishioka |
| 5,239,412 A | 8/1993 | Naka et al. | | 6,768,536 B2 | 7/2004 | Okuwaki et al. |
| D342,063 S | 12/1993 | Howitt et al. | | 6,774,871 B2 | 8/2004 | Birdwell |
| 5,306,926 A | 4/1994 | Yonemoto | | 6,778,246 B2 | 8/2004 | Sun et al. |
| 5,324,930 A | 6/1994 | Jech, Jr. | | 6,833,938 B2 | 12/2004 | Nishioka |
| D350,342 S | 9/1994 | Sack | | 6,840,619 B2 | 1/2005 | Dreher |
| 5,352,886 A | 10/1994 | Kane | | 6,851,805 B2 | 2/2005 | Blum et al. |
| 5,359,444 A | 10/1994 | Piosenka et al. | | 6,893,124 B1 | 5/2005 | Kurtin |
| 5,375,006 A | 12/1994 | Haas | | 6,902,271 B2 | 6/2005 | Perrott et al. |
| 5,382,986 A | 1/1995 | Black et al. | | 6,918,670 B2 | 7/2005 | Blum et al. |
| 5,386,308 A | 1/1995 | Michel et al. | | 6,948,818 B2 | 9/2005 | Williams et al. |
| 5,424,927 A | 6/1995 | Schaller et al. | | 6,951,391 B2 | 10/2005 | Morris et al. |
| 5,440,357 A | 8/1995 | Quaglia | | 6,986,579 B2 | 1/2006 | Blum et al. |
| 5,443,506 A | 8/1995 | Garabet | | 7,008,054 B1 | 3/2006 | Kurtin et al. |
| 5,451,766 A | 9/1995 | Van Berkel | | 7,009,757 B2 | 3/2006 | Nishioka et al. |
| 5,488,439 A | 1/1996 | Weltmann | | 7,019,890 B2 | 3/2006 | Meredith et al. |
| 5,522,323 A | 6/1996 | Richard | | 7,041,133 B1 | 5/2006 | Azar |
| 5,552,841 A | 9/1996 | Gallorini et al. | | 7,085,065 B2 | 8/2006 | Silver |
| 5,608,567 A * | 3/1997 | Grupp ......................... 359/275 | | 7,133,172 B2 | 11/2006 | Nishioka |
| 5,615,588 A | 4/1997 | Gottschald | | 7,209,097 B2 | 4/2007 | Suyama et al. |
| 5,654,786 A | 8/1997 | Bylander | | 2001/0055094 A1 | 12/2001 | Zhang |
| 5,668,620 A | 9/1997 | Kurtin et al. | | 2002/0140899 A1 | 10/2002 | Blum et al. |
| 5,682,223 A | 10/1997 | Menezes et al. | | 2002/0149739 A1 | 10/2002 | Perrott et al. |
| 5,683,457 A | 11/1997 | Gupta et al. | | 2002/0186346 A1 | 12/2002 | Stantz et al. |

| | | | |
|---|---|---|---|
| 2003/0018383 | A1 | 1/2003 | Azar |
| 2003/0151721 | A1 | 8/2003 | Lai et al. |
| 2003/0210377 | A1 | 11/2003 | Blum et al. |
| 2004/0008319 | A1 | 1/2004 | Lai et al. |
| 2004/0108971 | A1 | 6/2004 | Waldern et al. |
| 2004/0117011 | A1 | 6/2004 | Aharoni et al. |
| 2004/0130677 | A1 | 7/2004 | Liang et al. |
| 2004/0179280 | A1 | 9/2004 | Nishioka |
| 2004/0196435 | A1 | 10/2004 | Dick et al. |
| 2004/0246440 | A1 | 12/2004 | Andina et al. |
| 2005/0073739 | A1 | 4/2005 | Meredith |
| 2005/0124983 | A1 | 6/2005 | Frey et al. |
| 2006/0044510 | A1 | 3/2006 | Williams et al. |

FOREIGN PATENT DOCUMENTS

| | | |
|---|---|---|
| CN | 89113088 | 10/2001 |
| DE | 4223395 | 1/1994 |
| EP | 0154962 A2 | 9/1985 |
| EP | 0233104 A1 | 8/1987 |
| EP | 0237365 A1 | 9/1987 |
| GB | 2170613 A | 8/1986 |
| GB | 2169417 A | 7/1987 |
| JP | 55-076323 | 6/1980 |
| JP | 1 237610 | 9/1989 |
| JP | 05-100201 | 4/1993 |
| JP | 10366043 | 12/1998 |
| JP | 11352445 | 12/1998 |
| WO | WO 92/01417 | 2/1992 |
| WO | WO 98/27863 | 7/1998 |
| WO | WO 99/27334 | 6/1999 |
| WO | WO-03/050472 A1 | 6/2003 |
| WO | WO-03/068059 A2 | 8/2003 |
| WO | WO-2004/008169 A1 | 1/2004 |
| WO | WO-2004/015481 A1 | 2/2004 |
| WO | WO-2004-034095 A2 | 4/2004 |
| WO | WO-2004/072687 A2 | 8/2004 |

OTHER PUBLICATIONS

"Focusing by Electrical Modulation of Refraction in a Liquid Crystal Cell"; Stephen T. Kowell, et al., *Aplied Optics*, vol. 23, No. 2, Jan. 15, 1984, pp. 278-289.

"Vision Trhough a Liquid-Crystal Spatial Light Modulator"; Larry N. Thibos, et al., *Inpress*, Adaptive Optics Conference, Durham, United Kingdom, 1999.

"Requirements for Segmented Spatial Light Modulators for Deffraction-Limited Imageing Through Aberrated Eyes"; Larry N. Thibos, et al., *Inpress*, Adaptive Optics Conference, Durham, United Kingdom, 1999.

"Use of Liquid-Crystal Adaptive-Optics to Alter the Refractive State of the Eye"; Larry N. Thibos, et al., *Optometry and Vision Science*, vol. 74 No. 7, Jul. 1997.

"Electronic Spectacles for the 21st Century"; *Indiana Journal of Optometry*, vol. 2, No. 1, 1999.

"Adaptive Optics: Liquid Crystals Lower the Cost of Adaptive Optic"; M. Anderson, *Laser Focus World*, Dec. 1999, pp. 1-3.

"Control Optimization of Spherical Modal Liquid Crystal Lenses"; A.F. Naumov & G.D. Love, *Optics Express*, vol. 4, No. 9, Apr. 26, 2999, pp. 344-352.

"Liquid Crystal Adaptive Lenses with Modal Control"; A.F. Naumov & M.Yu Loktev, *Optics Letters*, vol. 23, No. 13, Jul. 1, 1998, pp. 992-994.

"Liquid Lenses Eye Commercial Breakthrough"; (Internet Article under "Optics.org") from *Opto & Laser*, Nov. 2003.

Bradley, Arthur; Profile: Larry N. Thibos, PhD., and Donald T Miller, PhD ; Indiana Journal of Optometry; Spring 1999; vol. 2, No. 1.

Davis, Robert A.; Computer Vision Syndrome- The Eyestrain Epidemic ; Review of Optomtery, Sep. 15, 1997.

Lazarus, Stuart M ; The Use of Yoked Base-Up and Base-In Prism for Reducing Eye Strain at the Computer, Journal of the American Optometric Association, Apr. 1996.

Eyecare Business, Oct. 1997.

\* cited by examiner

*Primary Examiner*—Jordan M Schwartz
(74) *Attorney, Agent, or Firm*—Pearl Cohen Zedek Latzer, LLP

(57) ABSTRACT

An electro-active spectacle lens is disclosed. The spectacle lens comprises a first substrate having a first outer region and first inner region, a first electrode layer disposed adjacent to the first inner region, the first electrode layer including an outer electrode region having a first conductivity and an inner electrode region having a second conductivity, the first conductivity being greater than the second conductivity, a second substrate having a second outer region and second inner region, a second electrode layer disposed adjacent to the second inner region, the second electrode layer having a third conductivity, and an electro-active cell disposed between the first electrode layer and the second electrode layer, the electro-active cell containing an electro-active material. The first outer region and second outer region are configurable for fitting the spectacle lens within a lens frame without altering the electro-active cell.

22 Claims, 11 Drawing Sheets

ELECTRO-ACTIVE SPECTACLE EMPLOYING MODAL LIQUID CRYSTAL LENSES

The present application claims priority to U.S. Provisional Application No. 60/536,238 filed Jan. 14, 2004. This application is also a continuation-in-part of U.S. patent application Ser. No. 10/664,112 filed Aug. 20, 2003, which claims the benefit of U.S. Provisional Application No. 60/404,657 filed Aug. 20, 2002. U.S. patent application Ser. No. 10/664,112 is also a continuation-in-part of U.S. patent application Ser. No. 10/422,128 filed Apr. 24, 2003 now U.S. Pat. No. 6,857,741, which claims the benefit of U.S. Provisional Application No. 60/375,028, filed Apr. 25, 2002, and which is a continuation-in-part of U.S. patent application Ser. No. 10/387,143, filed Mar. 12, 2003 now U.S. Pat No. 7,023,594, which claims the benefit of U.S. Provisional Application Nos. 60/363,549, filed Mar. 13, 2002 and 60/401,700, filed Aug. 7, 2002, and which is a continuation-in-part of U.S. patent application Ser. No. 10/281,204, filed Oct. 28, 2002 now U.S. Pat. No. 6,733,130 and Ser. No. 10/046,244, filed Jan. 16, 2002 now U.S. Pat. No. 6,871,951. U.S. patent application Ser. No. 10/281,204 is a continuation of U.S. Pat. No. 6,491,394, filed Jun. 23, 2000. U.S. patent application Ser. No. 10/046,244 claims the benefit of U.S. Provisional Application Nos. 60/261,805, filed Jan. 17, 2001, 60/331,419, filed Nov. 15, 2001, and 60/326,991, filed Oct. 5, 2001, and is a continuation-in-part of U.S. Pat. No. 6,491,391, filed Jun. 23, 2000, U.S. Pat. No. 6,491,394, filed Jun. 23, 2000, and U.S. Pat. No. 6,517,203, filed Jun. 23, 2000, and U.S. Pat. No. 6,619,799, filed Jun. 23, 2000, all of which claim priority to U.S. Provisional Application Nos. 60/142,053, filed Jul. 2, 1999, 60/143,626, filed Jul. 14, 1999, 60/147,813, filed Aug. 10, 1999, 60/150,545, filed Aug. 25, 1999, 60/150,564, filed Aug. 25, 1999, and 60/161,363, filed Oct. 26, 1999. All of the foregoing applications, provisional applications, and patents are herein incorporated by reference in their entirety.

BACKGROUND OF THE INVENTION

Modal liquid crystal lenses are switchable lenses with a continuous phase variation across the lens. Modal liquid crystal lenses have been described, for example, by A. F. Naumov in a publication entitled Control Optimization Of Spherical Modal Liquid Crystal Lenses, published in Optics Express (26 Apr. 1999/vol. 4, No 9). The basic design of a modal liquid crystal lens, according to Naumov, is illustrated in FIGS. 1*a* and 1*b*. FIG. 1*a* is a planar view of an illustrative electrode layer used in a modal liquid crystal lens, and FIG. 1*b* is a side sectional view of an illustrative modal liquid crystal lens. As shown in FIGS. 1*a* and 1*b*, modal liquid crystal lens 100 includes a control electrode 130, which consists of a low conductivity, or highly resistive layer of conductive material, such as indium-tin-oxide ("ITO"), for example. Control electrode 130 is surrounded by a highly conductive annular contact electrode 120, which is made from a conductive metal, such as silver, aluminum, copper, for example.

FIG. 1*b* illustrates the construction of modal liquid crystal lens 100. As described by Naumov, control electrode 130 generally has a relatively high resistance with a surface resistance of around a few MΩ/square. Ground electrode 160 is generally a highly conductive ITO layer with a surface resistance of about 50 to 200 Ω/square. The cell 150 containing the liquid crystal material is formed by the spacers 140 placed between the front substrate 110 and rear substrate 170. The modal liquid crystal lens 100 is operated by applying a voltage to the annular contact electrode 120. The voltage across the modal liquid crystal lens 100 decreases radially towards the center of the modal liquid crystal lens 100 because of the potential divider that is formed by the high resistance control electrode 130 and the capacitance of the liquid crystal layer 150. In response to the radially varying potential, the retardance of liquid crystal layer 150 changes. Thus, the optical path length through the liquid crystal layer 150 increases from the edge of the modal liquid crystal lens 100 towards the center thus producing a retarding profile across the modal liquid crystal lens 100. By controlling the voltage and frequency of the waveform applied to the annular contact electrode 120 the optical power of the modal liquid crystal lens 100 can be continuously adjusted over a range of a few Diopters, depending on the thickness of the liquid crystal layer 150.

While such modal liquid crystal lenses offer several advantages in terms of continuous optical power tuning and simplicity of design, they have several limitations that hinder their practical use as spectacle lenses, in particular, a lens for the treatment of presbyopia. For example, such lenses are not completely transparent, and use visible metallic electrodes. In addition, such lenses are not constructed in a manner that allows for them to be cut and shaped so that they may be placed within a frame. Moreover, such lenses do not have a relatively quick response time (for example, less than 30 milliseconds) so that the optical power changes faster than the wearer's eye can detect, and do not account for a step change in optical power with an adjacent base lens used to provide a distance correction. This leads to discomfort for the wearer, and also detracts from the cosmetic appearance of the lens.

Accordingly, the present invention provides an electro-active lens and electro-active spectacles useful in the treatment of presbyopia that employ modal liquid crystal lenses, and that overcome the disadvantages of known devices while offering features not present in known devices. Although certain deficiencies in the related art are described in this background discussion and elsewhere, it will be understood that these deficiencies were not necessarily heretofore recognized or known as deficiencies. Furthermore, it will be understood that, to the extent that one or more of the deficiencies described herein may be found in an embodiment of the claimed invention, the presence of such deficiencies does not detract from the novelty or non-obviousness of the invention or remove the embodiment from the scope of the claimed invention.

SUMMARY OF THE INVENTION

The invention, according to one embodiment, relates to an electro-active spectacle lens. The spectacle lens comprises a first substrate having a first outer region and first inner region, a first electrode layer disposed adjacent to the first inner region, the first electrode layer including an outer electrode region having a first conductivity and an inner electrode region having a second conductivity, the first conductivity being greater than the second conductivity, a second substrate having a second outer region and second inner region, a second electrode layer disposed adjacent to the second inner region, the second electrode layer having a third conductivity, and an electro-active cell disposed between the first electrode layer and the second electrode layer, the electro-active cell containing an electro-active material. The first outer region and second outer region are configurable for fitting the spectacle lens within a lens frame without altering the electro-active cell.

The invention, according to another embodiment, relates to an electro-active spectacle lens. The electro-active spectacle lens comprises a first modal liquid crystal lens assembly having a first substrate having a first outer region and first inner region, a first electrode layer disposed adjacent to the first inner region, the first electrode layer including a first outer electrode region having a first conductivity and a first inner electrode region having a second conductivity, the first conductivity being greater than the second conductivity, a second substrate having a second outer region and second inner region, a second electrode layer disposed adjacent to the second inner region, the second electrode layer having a third conductivity, and a first electro-active cell disposed between the first electrode layer and the second electrode layer, the first electro-active cell containing a first electro-active material. The electro-active spectacle lens further comprises a second modal liquid crystal lens assembly having a third substrate having a third outer region and third inner region, a third electrode layer disposed adjacent to the third inner region, the third electrode layer including a second outer electrode region having a fourth conductivity and a second inner electrode region having a fifth conductivity, the fourth conductivity being greater than the fifth conductivity, a fourth substrate having a fourth outer region and fourth inner region, a fourth electrode layer disposed adjacent to the fourth inner region, the fourth electrode layer having a sixth conductivity, and a second electro-active cell disposed between the third electrode layer and the fourth electrode layer, the second electro-active cell containing a second electro-active material, and a controller for directing application of voltage to the first electrode layer, second electrode layer, third electrode layer and fourth electrode layer.

BRIEF DESCRIPTION OF THE DRAWINGS

The present invention can be more fully understood by reading the following detailed description of the presently preferred embodiments together with the accompanying drawings, in which like reference indicators are used to designate like elements, and in which.

DETAILED DESCRIPTION OF PREFERRED EMBODIMENTS

Figure 1A:
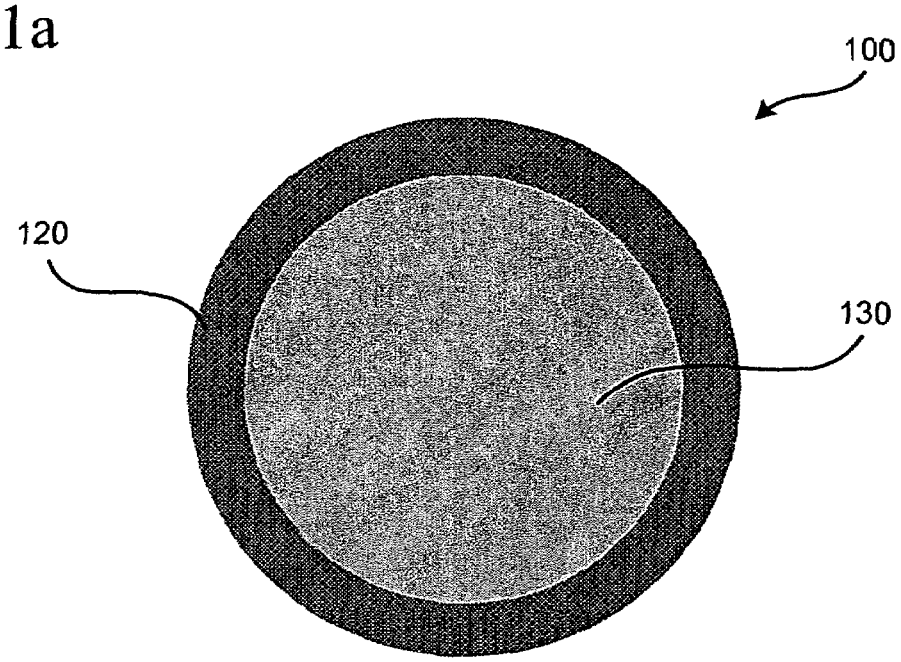
FIG. 1a is a planar view of an illustrative electrode layer used in a modal liquid crystal lens.
Figure 1B:
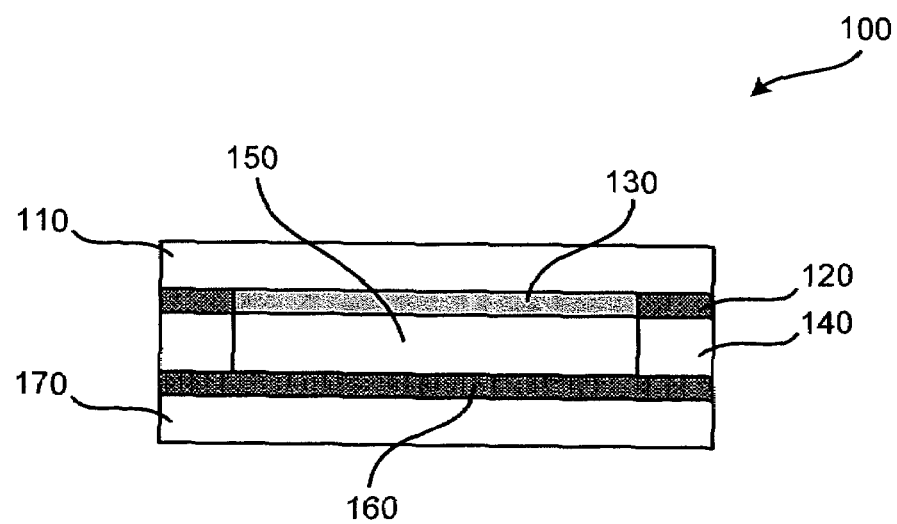
FIG. 1b is a side sectional view of an illustrative modal liquid crystal lens.

Various embodiments of electro-active spectacle lenses and spectacles employing modal liquid crystal lens assemblies, and methods of manufacturing such electro-active spectacles lenses are described herein. These lenses may be used to provide vision correction for one or more focal lengths, and may further correct non-conventional refractive error including higher order aberrations.

To assist with understanding certain embodiments described herein, explanations of various terms are provided. "Attaching" can include bonding, depositing, adhering, and other well-known attachment methods. A "controller" can include or be included in a processor, a microprocessor, an integrated circuit, a computer chip, and/or a chip. A "conductive bus" operates to conduct data in the form of an electrical signal from one place to another place. "Near distance refractive error" can include presbyopia and any other refractive error needed to be corrected for one to see clearly at near distance. "Intermediate distance refractive error" can include the degree of presbyopia needed to be corrected an intermediate distance and any other refractive error needed to be corrected for one to see clearly at intermediate distance. "Far distance refractive error" can include any refractive error needed to be corrected for one to see clearly at far distance. "Conventional refractive error" can include myopia, hyperopia, astigmatism, and/or presbyopia. "Non-conventional refractive error" can include irregular astigmatism, aberrations of the ocular system including coma, chromatic aberrations, and spherical aberrations, as well as any other higher order aberrations or refractive error not included in conventional refractive error. "Optical refractive error" can include any aberrations associated with a lens optic.

In certain embodiments, a "spectacle" can include one lens. In other embodiments, a "spectacle" can include more than one lens. A "multi-focal" lens can include bifocal, trifocal, quadrafocal, and/or progressive addition lens. A "finished" lens blank can include a lens blank that has finished optical surface on both sides. A "semi-finished" lens blank can include a lens blank that has, on one side only, a finished optical surface, and on the other side, a non-optically finished surface, the lens needing further modifications, such as, for example, grinding and/or polishing, to make it into a useable lens. An "unfinished" lens blank has no finished surface on either side. "Base lens" refers to the non-electro-active portion of a lens blank which has been finished.

"Surfacing" can include grinding and/or polishing off excess material to finish a non-finished surface of a semi-finished or unfinished lens blank. The lens blank may also be finished using free form machining techniques that have recently been adopted by the ophthalmic lens industry. Free forming techniques allow a completely arbitrary shape to be placed on the lens blank that may be used to complete conventional error correction, but may also be used to correct higher order aberrations to provide for a non-conventional error correction that may lead to vision correction better than 20/20. Further, the lens blank can be fabricated by bonding two or more lens wafers together to form a finished lens or a semi-finished lens blank. It should be appreciated that the lens blank, whether finished, unfinished, or semi-finished, may initially be fabricated using free form techniques to correct for either or both of conventional and non-conventional refractive error.

Modal liquid crystal lenses are switchable lenses with a continuous phase variation across the lens. Such lenses are operated by applying a voltage to an annular contact electrode. Voltage across the lens decreases radially towards its center because of the potential divider caused by the high resistance control electrode and the capacitance of the liquid crystal layer. This changes the retardance of liquid crystal layer, and increases the optical path length through the liquid crystal layer from the edge of the lens towards the center, thus producing a retarding profile across the lens. However, known modal liquid crystal lenses have several limitations that hinder their practical use as spectacle lenses, i.e., they are not completely transparent, they cannot be cut or shaped, they do not have a relatively quick response time and do not account for a step change in optical power with an adjacent base lens used to provide a distance correction.

Figure 2A:
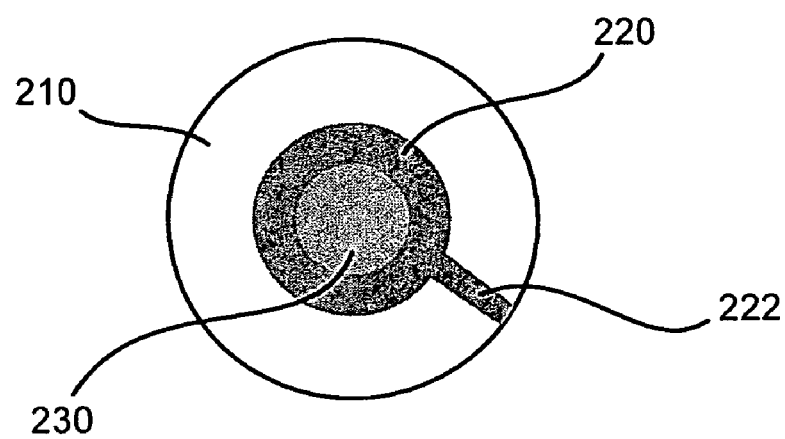
FIGS. 2a, 2b, 2c and 2d illustrate the various components of an illustrative electro-active spectacle lens in accordance with one embodiment of the invention.

FIGS. 2a, 2b, 2c and 2d illustrate the various components of an illustrative electro-active spectacle lens in accordance with one embodiment of the invention. FIG. 2a is planar view of a front substrate 210 with a first electrode layer including annular contact electrode 220 and control electrode 230. Front substrate 210 is comprised of glass, optical grade plastic or other suitable material. Control electrode 230 is comprised of a low conductivity, or highly resistive layer, transparent material, and annular contact electrode 220 is formed from a highly conductive, transparent material. In one embodiment, the control electrode 230 and annular contact electrode 220 are formed from ITO, and it should be appreciated that the characteristics of the ITO used for the control electrode 230 and annular contact electrode 220 may be varied to achieve the desired conductivity for in the different electrodes. Bus electrode 222 is also placed on front substrate 210 and coupled to annular contact electrode 220. In one embodiment, bus electrode 222 is formed from highly conductive, transparent material, such as ITO, for example. As shown in FIG. 2a, bus electrode 222 extends from the edge of front substrate 210 to annular contact electrode 220 so that power can be applied to the annular contact electrode 220 from the edge of front substrate 210, and eventually, from the edge of the finished lens 200.

Figure 2B:
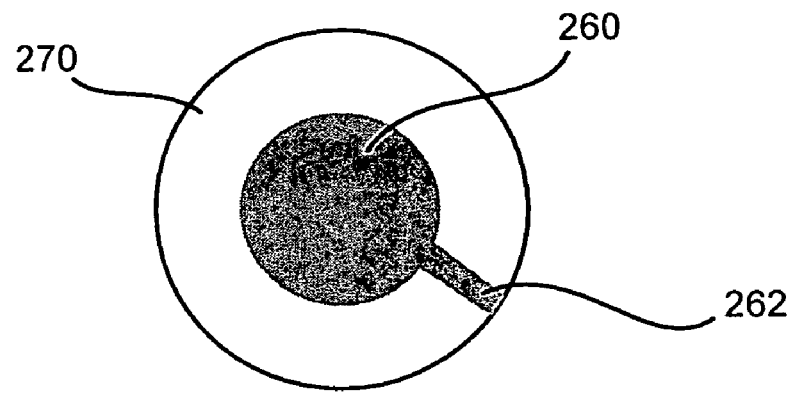

FIG. 2b is planar view of a rear substrate 270 with a second electrode layer including ground electrode 260. In one embodiment, ground electrode 260 is formed from highly conductive, transparent material, such as ITO, for example. Bus electrode 262 is also placed on rear substrate 270 and coupled to ground electrode 260. In one embodiment, bus electrode 262 is formed from highly conductive, transparent material, such as ITO, for example. As shown in FIG. 2b, bus electrode 262 extends from the edge of rear substrate 270 to ground electrode 260 so that electrical contact can be made to the ground electrode 260 from the edge of rear substrate 270, and eventually, from the edge of the finished lens 200.

Figure 2C:
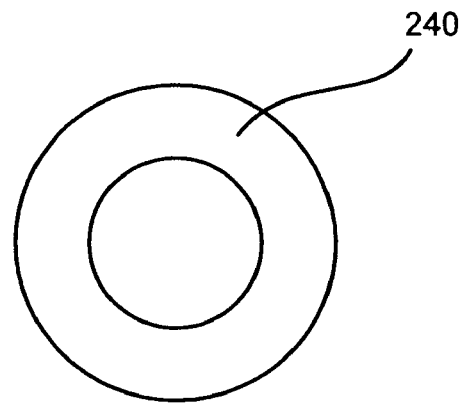

FIG. 2c is a planar view of an illustrative spacer ring 240. In one embodiment, spacer ring 240 is formed from ultra thin plastic, glass sheet or other suitable transparent materials. Spacer ring 240 may be attached to either the front substrate 210 or rear substrate 270. Spacer ring 240 will generally have a thickness in the range of about 5 to 25 microns. It should be appreciated that, in alternative embodiments, an electro-active spectacles lens may avoid the use of a spacer ring by machining a recess in one or both of the front and rear substrates prior to depositing the electrodes layers. It should further be understood, that if nematic liquid crystals are used, then two cells with mutually orthogonal orientations will be required to deal with birefringence.

Figure 2D:
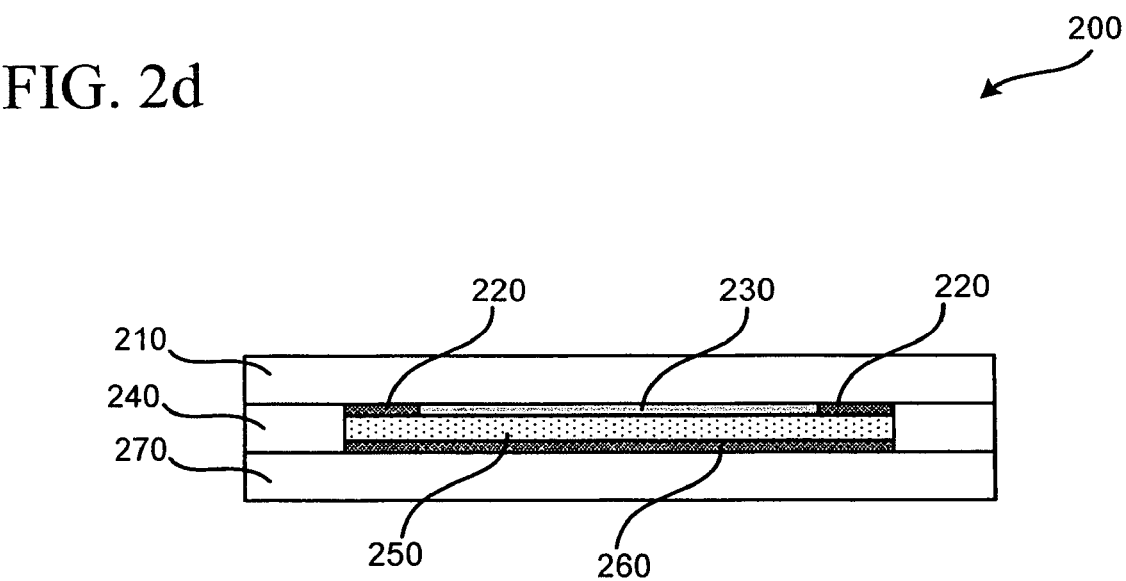

FIG. 2d is a side sectional view of an illustrative electro-active spectacle lens assembling the components illustrated in FIGS. 2a, 2b and 2c. As shown in FIG. 2d, electro-active spectacle lens 200 is comprised of front substrate 210, spacer ring 240, and rear substrate 270. As described above, the first electrode layer including annular contact electrode 220 and control electrode 230 is disposed adjacent to front substrate 210. The second electrode layer including the ground electrode 260 is disposed adjacent to the rear substrate 270. Spacer ring 240 is disposed between front substrate 210 and rear substrate 270, and the bore in spacer ring 240 is enclosed. This interior space is filled with electro-active material and forms an electro-active cell 250.

It should be appreciated that various electro-active materials may be employed in the electro-active spectacle lenses of the present invention, including those disclosed in commonly assigned U.S. patent application Ser. No. 10/046,244 filed Jan. 16, 2002, Ser. No. 10/387,143 filed Mar. 12, 2003, Ser. No. 10/422,128 filed Apr. 24, 2003, and Ser. No. 10/664,112 filed Aug. 20, 2003, the contents of which all of the foregoing applications are incorporated by reference in their entirety.

Referring to FIG. 2d, as assembled, annular contact electrode 220, control electrode 230 and ground electrode 260 are disposed adjacent to the electro-active cell 250. Alignment layers (not illustrated) are formed over the annular contact electrode 220, control electrode 230 and ground electrode 260 in the area where the electro-active material will reside within the electro-active cell 250. It should be appreciated that alignment layers may be formed from Poly Vinyl Alcohol (PVA) or other suitable materials. Other suitable methods and process for utilizing alignment layers formed on electrodes may also be employed, such as those described U.S. patent application Ser. No. 10/046,244, Ser. No. 10/387,143, Ser. No. 10/422,128, and Ser. No. 10/664,112, the contents of which are incorporated by reference in their entirety.

Figure 3A:
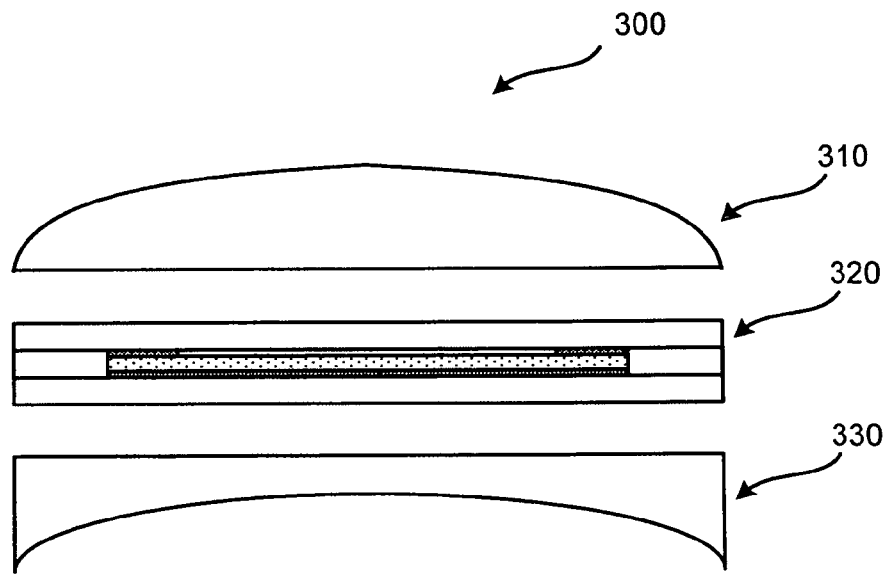
FIGS. 3a and 3b are side sectional views (exploded and assembled, respectively) of an illustrative electro-active spectacle lens including a modal liquid crystal lens assembly in accordance with one embodiment of the invention.
Figure 3B:
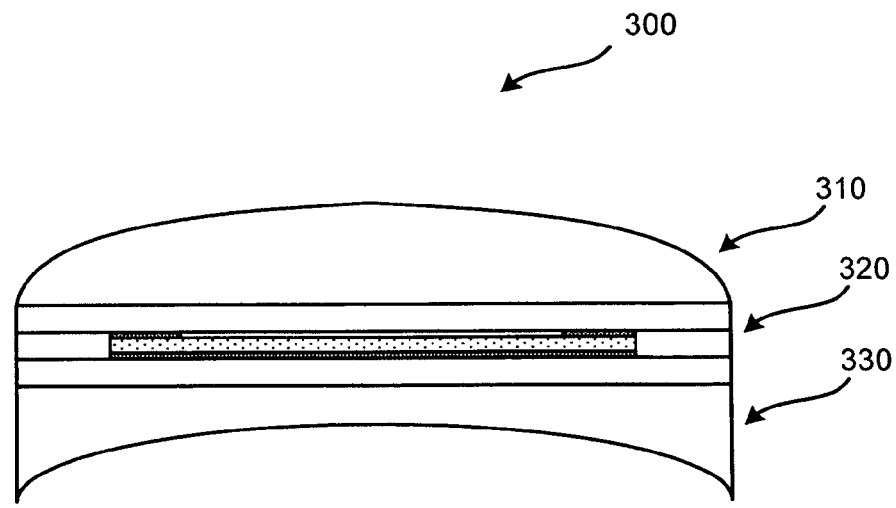

FIGS. 3a and 3b are side sectional views (exploded and assembled, respectively) of an illustrative electro-active spectacle lens including a modal liquid crystal lens assembly in accordance with one embodiment of the invention. As shown in exploded view in FIG. 3a, spectacle lens 300 is comprised of first base lens 310, modal liquid crystal lens assembly 320, and second base lens 330. In this embodiment, modal liquid crystal lens assembly 320 shares the same features and structure of electro-active spectacles lens 200 described above. Modal liquid crystal lens assembly 320 is disposed between first base lens 310 and second base lens 330, which in this embodiment, are lens wafers that produce the base optical power of the spectacle lens 300, as shown assembled in FIG. 3b. Modal liquid crystal lens assembly 320 may be bonded between first base lens 310 and second base lens 330 with thermal or optically cured resins or adhesives, or other suitable materials. It should further be appreciated that other suitable methods of attaching the modal liquid crystal lens assembly and base lenses may be employed as desired by the skilled artisan. In one embodiment, the index of refraction of the substrates used in the modal liquid crystal lens assembly, the base lenses, and the adhesives or resins fall within a predetermined range from one another, or differ by no more than a specific tolerance. For example, in some embodiments, these materials may have indices of refraction that differ by no more than about 0.01 to 0.05.

Figure 4A:
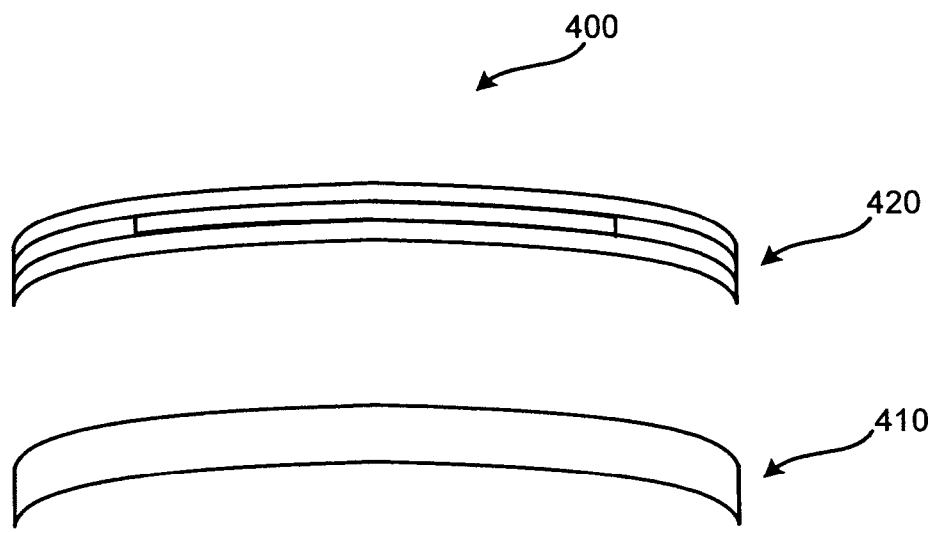
FIGS. 4a and 4b are side sectional views (exploded and assembled, respectively) of an illustrative electro-active spectacle lens including a modal liquid crystal lens assembly in accordance with one embodiment of the invention.
Figure 4B:
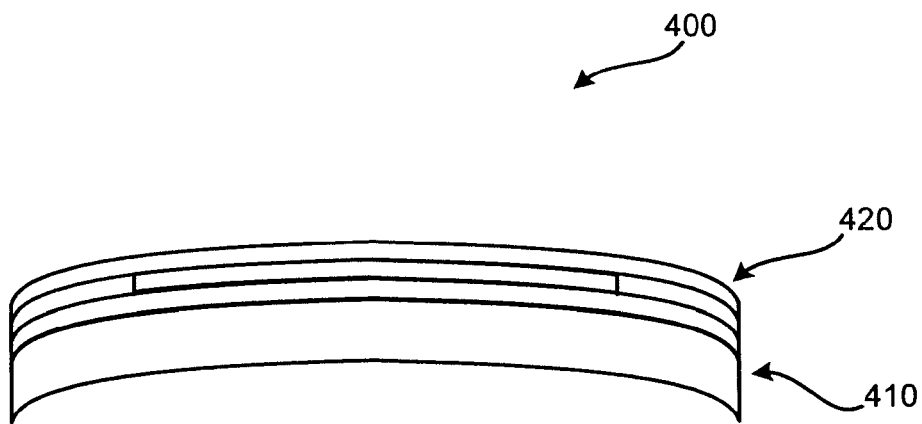

FIGS. 4a and 4b are side sectional views (exploded and assembled, respectively) of an illustrative electro-active spectacle lens including a modal liquid crystal lens assembly in accordance with one embodiment of the invention. As shown in exploded view in FIG. 4a, spectacle lens 400 is comprised of first base lens 410 and modal liquid crystal lens assembly 420. In this embodiment, modal liquid crystal lens assembly 420 shares many of the same features and structure of electro-active spectacles lens 200 described above, except that modal liquid crystal lens assembly 420 is formed with curved front and rear substrates, and spacer ring. Modal liquid crystal lens assembly 420 may be bonded or attached to first base lens 410 in any suitable manner, such as that described above with reference to spectacle lens 300. In an alternate embodiment, the positioning of the base lens and modal liquid crystal lens assembly may be reversed. In addition, although spectacle lens 400 is shown with only first base lens 410, additional base lenses may be employed in alternate curved spectacle lens embodiments.

Figure 5A:
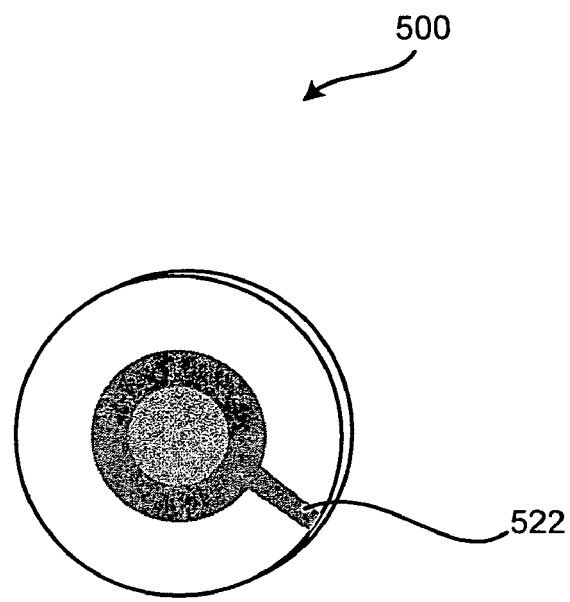
FIGS. 5a, 5b, 5c and 5d are perspective views of an illustrate electro-active spectacles lens in further detail demonstrating an illustrative finishing process for placing the electro-active spectacles lens in an eyeglass frame in accordance with an embodiment of the invention.
Figure 5B:
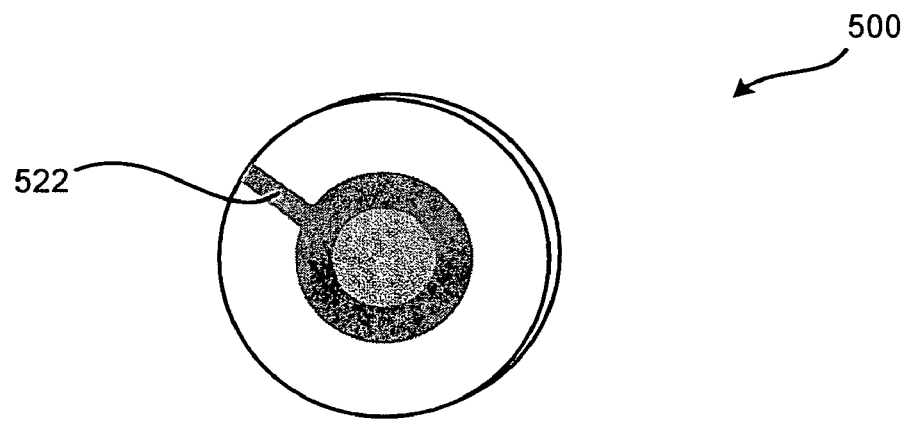
Figure 5C:
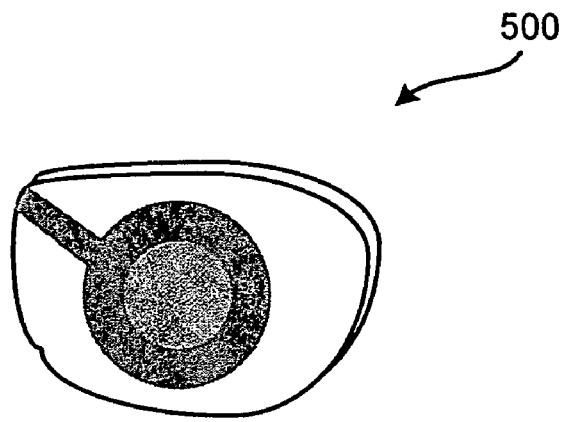
Figure 5D:
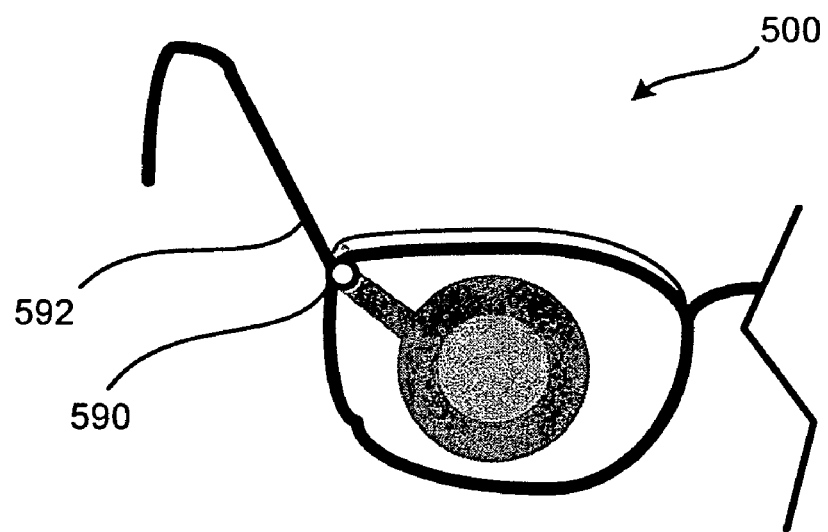

FIGS. 5a, 5b, 5c and 5d are perspective views of an illustrate electro-active spectacles lens in further detail demonstrating an illustrative finishing process for placing the electro-active spectacles lens in an eyeglass frame in accordance with an embodiment of the invention. As shown in FIG. 5a, electro-active spectacle lens 500 is provided. In this embodiment, electro-active spectacle lens 500 shares the same features and structure of electro-active spectacles lens 200 described above, including a bus electrode 522. As shown in FIG. 5b, electro-active spectacle lens 500 may be rotated to position bus electrode 522 so that electrical contacts can be made in the appropriate eyeglass frame. In some embodiments in which electro-active spectacle lens 500 is a toric lens possessing cylinder power for the correction of astigmatism, then the frame design and the required axis of the cylinder correction for electro-active spectacle lens 500 will need to be taken into account when fabricating the electro-active spectacle lens 500. As shown in FIGS. 5c and 5d, electro-active spectacle lens 500 is edged and shaped so that it may be placed in a particular eyeglass frame 592 and appropriate contact can be made with electrical contacts 590.

Further detail on suitable methods and process for edging spectacle lenses, finishing blanks into lenses, machining lenses, and manufacturing the components of said lenses in general is disclosed in commonly assigned U.S. patent application Ser. No. 10/046,244, Ser. No. 10/387,143, Ser. No. 10/422,128, and Ser. No. 10/664,112, the contents of which are incorporated by reference in their entirety.

Figure 6A:
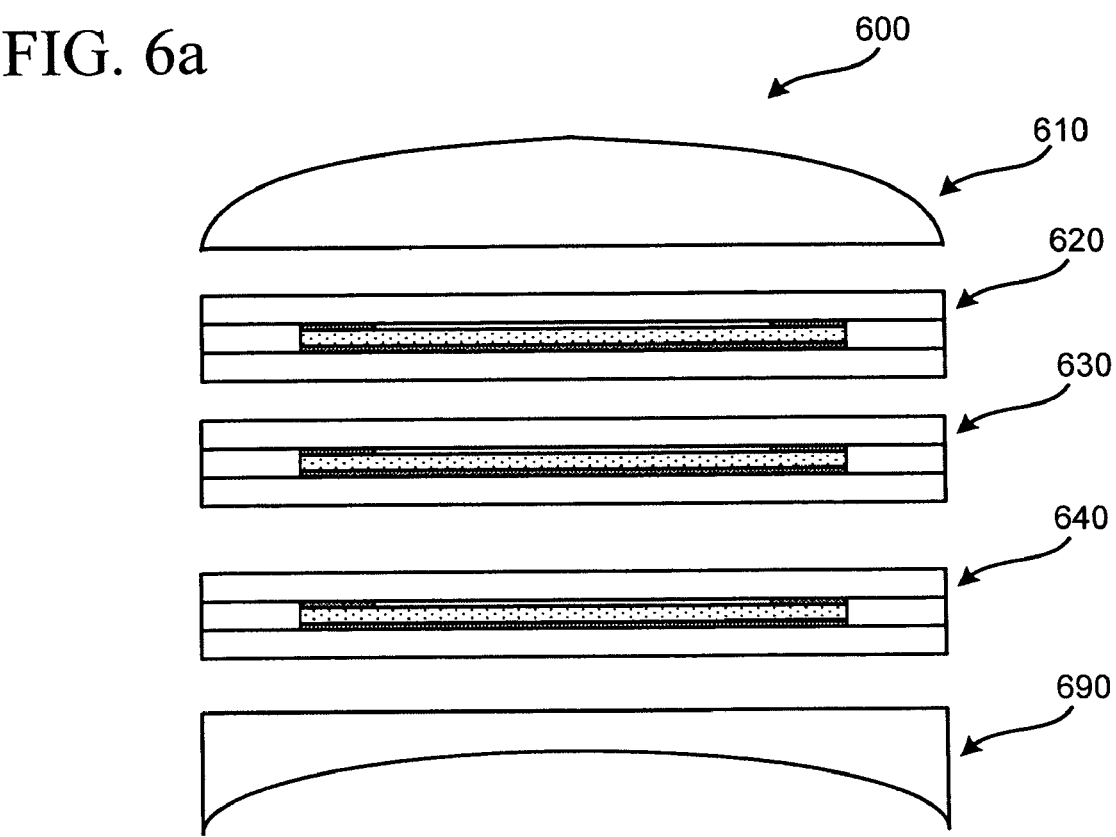
FIGS. 6a and 6b are side sectional views (exploded and assembled, respectively) of an illustrative electro-active spectacle lens including a plurality of modal liquid crystal lens assemblies in accordance with one embodiment of the invention.
Figure 6B:
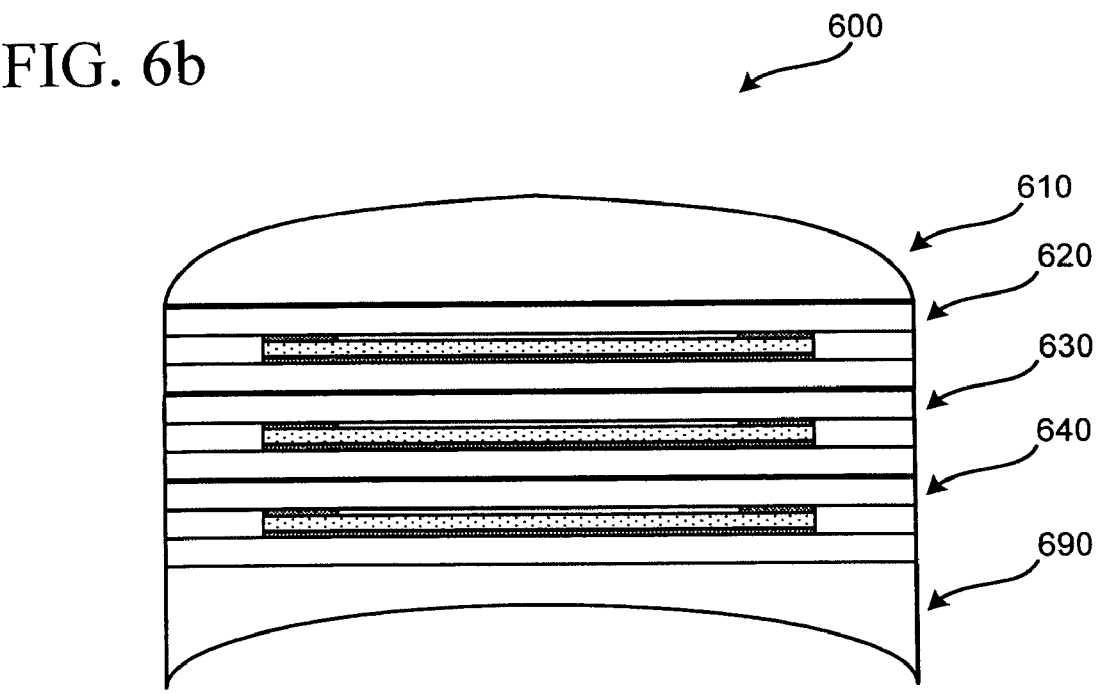

FIGS. 6a and 6b are side sectional views (exploded and assembled, respectively) of an illustrative electro-active spectacle lens including a plurality of modal liquid crystal lens assemblies in accordance with one embodiment of the invention. As shown in exploded view in FIG. 6a, spectacle lens 600 is comprised of first base lens 610, first modal liquid crystal lens assembly 620, second modal liquid crystal lens assembly 630, third modal liquid crystal lens assembly 640, and second base lens 690. In this embodiment, modal liquid crystal lens assemblies 620, 630, 640 each share the same features and structure of electro-active spectacles lens 200 described above. Modal liquid crystal lens assemblies 620, 630, 640 are disposed between first base lens 610 and second base lens 690, which in this embodiment are lens wafers that produce the base optical power of the spectacle lens 600, as shown assembled in FIG. 6b. Modal liquid crystal lens assemblies 620, 630, 640 may be bonded between first base lens 610 and second base lens 690 with thermal or optically cured resins or adhesives, or other suitable materials. It should further be appreciated that other suitable methods of attaching the modal liquid crystal lens assemblies and base lenses may be employed as desired by the skilled artisan.

In this embodiment employing a plurality of stacked modal liquid crystal lens assemblies, the skilled artisan can achieve a number of objectives. For example, the use of multiple, stacked modal liquid crystal lens assemblies reduces the switching time for the combined electro-active spectacle lens. This may be accomplished by reducing the optical power that each modal liquid crystal lens assembly would need to produce, which in turn reduces the required thickness of the electro-active cell and increases the overall switching speed of the electro-active spectacle lens. For example, three stacked modal liquid crystal lens assemblies (as shown in FIG. 6b) each producing +1.0 Diopters of optical power could replace a modal liquid crystal lens assembly producing +3.0 Diopters of adjustable optical power. The use of stacked modal liquid crystal lens assemblies also allows the user to address birefringence. For example, by cross-orienting the liquid crystal alignment axes of stacked modal liquid crystal lens assemblies, a device can be produced that is polarization insensitive. In alternate embodiments, cholesteric liquid crystals may be employed to address birefringence, as opposed to using additional assemblies.

Another application of the inventive design in FIG. 6 would be to provide a single manufacturing design of a bifocal lens for multiple prescriptions. As shown in FIG. 6b, three stacked, modal liquid crystal lens assemblies, each with a adjustable range of from about 0.0 to +1.0 Diopter of optical power, could be used in a "ganged" fashion to continuously provide desired amounts of optical power ranging from about 0.0 to +3.0 Diopters. For example, a patient that requires a +1.0 Diopter presbyope prescription may need only a single modal liquid crystal lens assembly activated to provide a +1.0 Diopter of optical power. Moreover, a +1.5 Diopter presbyope may have two modal liquid crystal lens assemblies activated at +0.75 Diopters each, or one lens at +1.0 Diopter and another at +0.5 Diopter, or other suitable combinations arriving at the desired optical power. Similarly, a +2.5 Diopter presbyope may have two modal liquid crystal lens assemblies activated at +1.0 Diopter and the third at +0.5 Diopter, while a +3.0 Diopter presbyope may have all three modal liquid crystal lens assemblies activated to their maximum power.

Such an embodiment would allow for a single add power combination of a spectacle design to be manufactured for the vast majority if not all of the presbyopic market, reducing the number of individual stock units that have to be manufactured and stored. Additionally, a presbyope would only need a single pair of spectacles as he/she aged and lost accommodation ability, unless there was a distance correction power change. As one requires more add power, the controller that sets the applied voltage to the electro-active spectacle lenses could be adjusted to provide higher plus power with the same set of spectacles as the wearer aged, for example.

Further detail on structuring electro-active lenses in a stacked arrangement or fashion is disclosed in commonly assigned U.S. application Ser. No. 10/046,244, Ser. No. 10/387,143, Ser. No. 10/422,128, and Ser. No. 10/664,112, the contents of which are incorporated by reference in their entirety.

Figure 7:
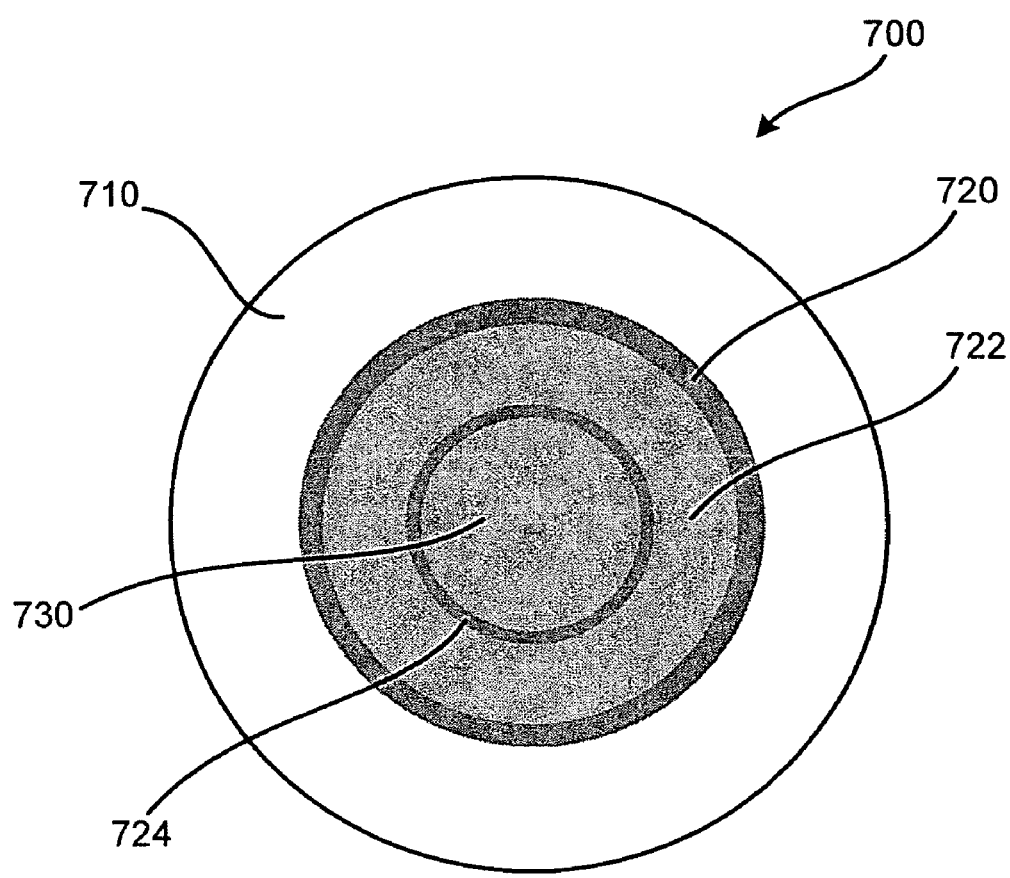
FIG. 7 is planar view of an illustrative electro-active spectacle lens that employs an electro-active blending zone through the addition of a blended electrode.

As stated above, a significant change in optical power from one region of the electro-active spectacle lens to another adjacent region can cause wearer discomfort. Image jump and discontinuity between vision correction regions or zones may be lessened through the use of an electro-active blending zone. FIG. 7 is planar view of an illustrative electro-active spectacle lens 700 that employs an electro-active blending zone through the addition of a blended electrode 722. Electro-active spectacle lens 700, as shown in FIG. 7, includes front substrate 710 with a first electrode layer including outer annular contact electrode 720, blended electrode 722, inner annular contact electrode 724 and control electrode 730. In some embodiments, outer annular contact electrode 720 and inner annular contact electrode 724 share many of the same features and structure as annular contact electrode 220 described above. Similarly, control electrode 730 share many of the same features and structure as control electrode 230 described above. Blended electrode 722 is formed of graded resistivity, transparent material, such as ITO, for example, that includes a tapered resistance to create a voltage profile that would smooth the optical power from the edges of the blending zone. Alternatively, the blend electrode may be of constant conductivity, but merely driven by the appropriate voltage and frequency to produce a optical power gradient.

Figure 8:
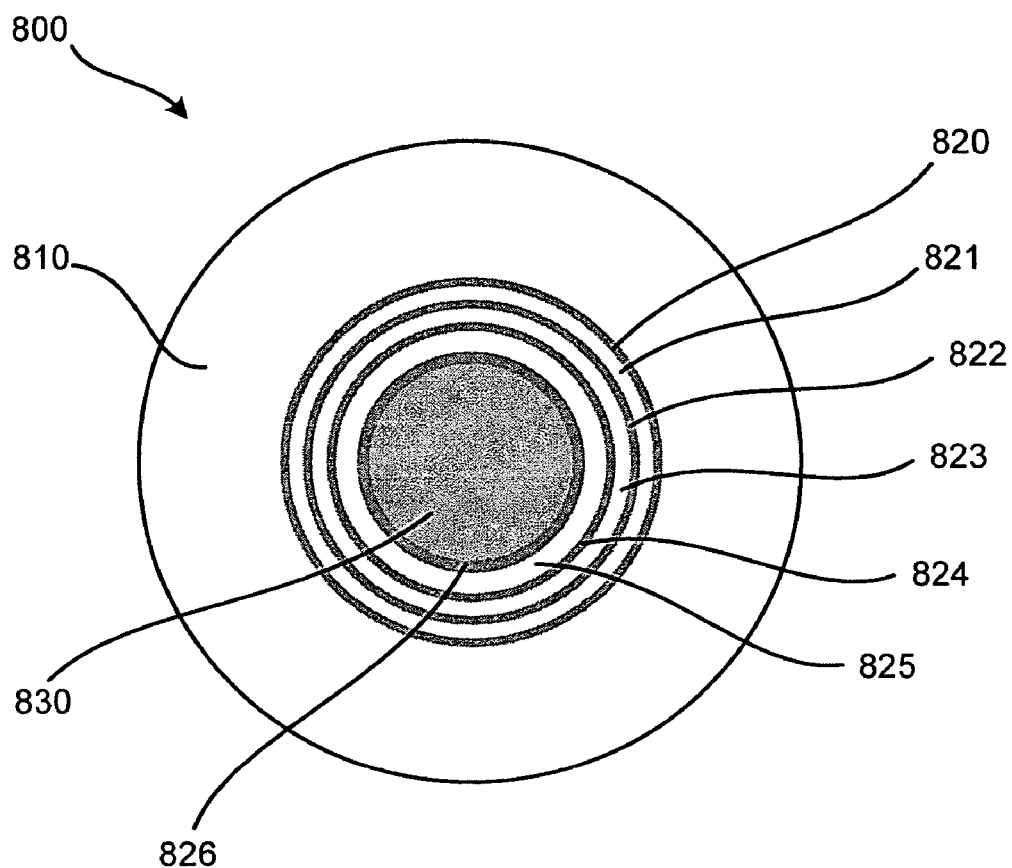
FIG. 8 is planar view of an illustrative electro-active spectacle lens that employs a series of electro-active blending zones through the addition of blended electrodes.

In an alternate embodiment, as shown in FIG. 8, a series of alternating concentric ring electrodes, switching between annular contact electrodes 820, 822, 824, 826 and blended electrodes 821, 823; 825 may be utilized in an electro-active spectacle lens 800 to create an optical power transition that minimizes the abrupt change in power that would be present in the associated electro-active cell. It should be appreciated that in such embodiments, where the number of concentric electrodes is increased, area requirements may demand that the area of the electro-active cell also be extended in diameter so the additional electrodes could act on the electro-active material to produce a power transition. Moreover, since the electro-active spectacle lens is dynamically and continuously adjustable over its allowed range, the transition zone would have to be voltage-tunable as well, to allow for a blended transition that matches the corrective power of the two regions at their boundary.

Figure 9A:
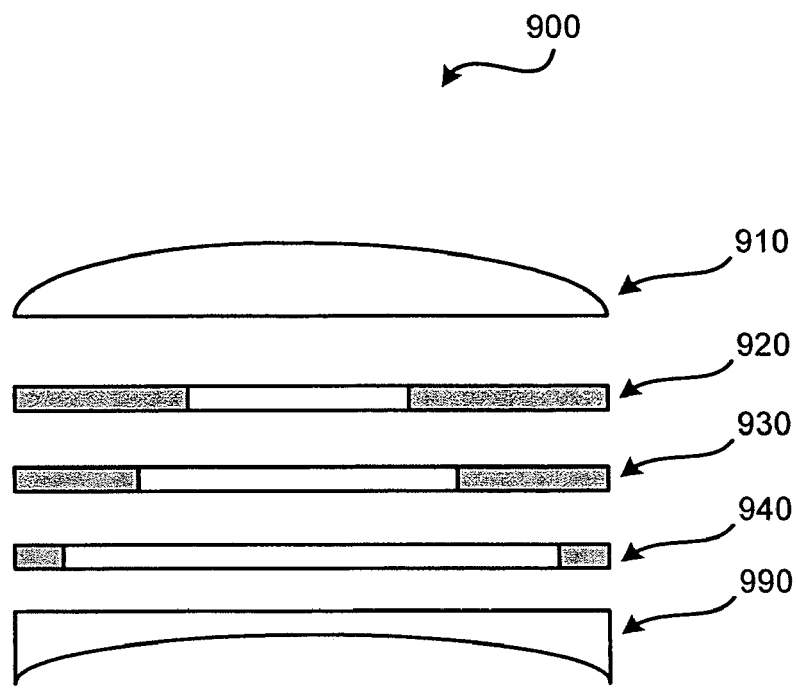
FIGS. 9a and 9b are side sectional views (exploded and assembled, respectively) of an illustrative electro-active spectacle lens including a plurality of modal liquid crystal lens assemblies in accordance with one embodiment of the invention.
Figure 9B:
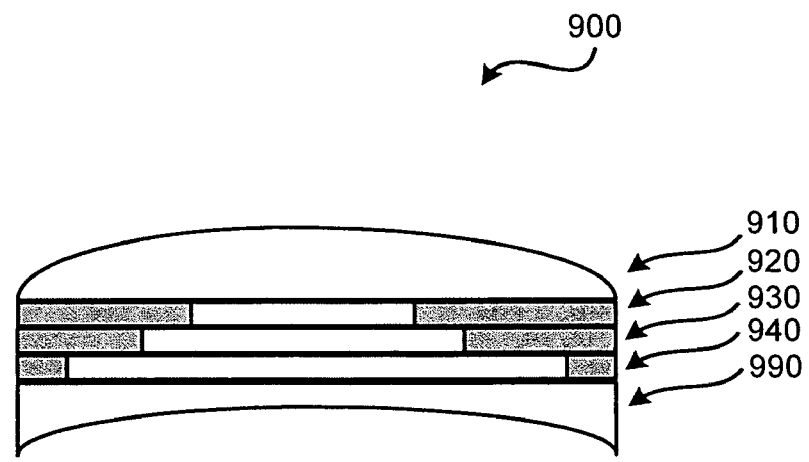

In an alternate embodiment, a series of stacked modal liquid crystal lens assemblies having electro-active cells of varying diameter may be employed to achieve a blended transition of optical power. FIGS. 9a and 9b are side sectional views (exploded and assembled, respectively) of an illustrative electro-active spectacle lens including a plurality of modal liquid crystal lens assemblies in accordance with one embodiment of the invention. As shown in exploded view in FIG. 6a, spectacle lens 900 is comprised of first base lens 910, first modal liquid crystal lens assembly 920, second modal liquid crystal lens assembly 930, third modal liquid crystal lens assembly 940, and second base lens 990. In this embodiment, modal liquid crystal lens assemblies 920, 930, 940 each share the same features and structure of electro-active spectacles lens 200 described above, except that the diameter of the electro-active cell region varies in each lens assembly. Each lens assembly 920, 930, 940 may, for example, have up to +1.0 Diopter of optical power such that lens 900 may be capable of providing a total of +3.0 Diopter of power in the region defined by the smallest electro-active cell, i.e., in lens assembly 920.

The annular region between the smallest and the middle lens radii would have +2.0 Diopters and the annular region between the middle and largest lens radii would have just +1.0 Diopter of power, providing a graduated power decrease to yield a blending transition of optical power. In addition to providing a cosmetically pleasing blend, a transition zone could also be used to provide intermediate vision focusing in an annular region around the central reading portion of the lens assembly but interior to the distance correction region, thus creating a trifocal effect. It should be appreciated that any suitable number of annular regions or zones and corresponding electrodes may be employed to achieve the desired blending transition or focal change or cosmetic appearance for the electro-active spectacle lens.

In still other embodiments, the actual optical power profile within in the modal lens may be shaped by applying the appropriate voltage and frequency to the driving electrode such that a slight roll off in optical power will occur near the edge of the modal lens. This can be used alone or in combination with stacking to produce more optical blending of the power zones.

Further detail on utilizing electro-active blending zones in electro-active lenses is disclosed in commonly assigned U.S. application Ser. No. 10/046,244, Ser. No. 10/387,143, Ser. No. 10/422,128, and Ser. No. 10/664,112, the contents of which are incorporated by reference in their entirety.

It should further be appreciated that the electro-active spectacle lenses of the present invention may be employed in combination with structural components or vision correction devices disclosed in the foregoing applications, such as the controller or processor for controlling the voltage applied to the various electrodes, memory for storing information for controlling the electro-active lens, power supply or batteries, electrical contacts and switches, rangefinders or view sensor devices, all of which have been incorporated by reference previously herein. Further detail on the control and operation of electro-active spectacle lenses is also found in the foregoing applications.

While the foregoing description includes details and specificities, it is to be understood that these have been included for purposes of explanation only, and are not to be interpreted as limitations of the present invention. Modifications to the embodiments described above can be made without departing from the spirit and scope of the invention, which is intended to be encompassed by the following claims and their legal equivalents.

What is claimed is:

1. An electro-active spectacle lens comprising:
a plurality of modal liquid crystal cells, each modal liquid crystal cell having a first electrode layer with outer and inner electrode regions with the conductivity of the outer electrode region greater than the conductivity of the inner electrode region and a second electrode layer having a third conductivity and an electro-active material between the first and second electrode layers, wherein each of the plurality of modal liquid crystal cells are in electrical communication with one of a plurality of electrode layers, wherein the electrode layers are adapted for altering the optical power of the spectacle lens and are all spaced from a peripheral edge of the spectacle lens.

2. The electro-active spectacle lens of claim 1, wherein at least two of the electrode layers are adapted to produce a retardance profile across one of the modal liquid crystal cells in response to an applied voltage.

3. The electro-active spectacle lens of claim 1, wherein at least two of the electrode layers are adapted to produce spherical power across one of the modal liquid crystal cells in response to an applied voltage.

4. The electro-active spectacle lens of claim 1, further comprising at least two bus electrodes respectively coupled to at least two of the electrode layers.

5. The electro-active spectacle lens of claim 1, further comprising a controller for directing application of voltage to each of the electrode layers.

6. The electro-active spectacle lens of claim 1, further comprising a spacer ring disposed between at least two of the plurality of modal liquid crystal cells.

7. The electro-active spectacle lens of claim 1, further comprising a base lens attached to one of the plurality of modal liquid crystal cells.

8. The electro-active spectacle lens of claim 1, further comprising a base lens.

9. The electro-active spectacle lens of claim 1, wherein the spectacle lens is configured in a stacked arrangement.

10. The electro-active spectacle lens of claim 1, wherein at least one of the electrode layers is located at an outer portion of said spectacle lens and further comprises a blended region having a graded conductivity that decreases radially from the outer portion of the spectacle lens.

11. The electro-active spectacle lens of claim 10, comprising electrode layers located at a the outer portion of the spectacle lens and an electrode layer located radially distant from the the outer portion, wherein the graded conductivity of the blended region falls within a range that is lesser than conductivity of one of the electrode layers at the the outer portion of the spectacle lens and greater than the conductivity of an electrode layer radially distal from the the outer portion.

12. An electro-active spectacle lens comprising:
- a plurality of modal liquid crystal cells in electrical communication with one of a plurality of electrode layers, each modal liquid crystal cell having a first electrode layer with outer and inner electrode regions with the conductivity of the outer electrode region greater than the conductivity of the inner electrode region and a second electrode layer having a third conductivity and an electro-active material between the first and second electrode layers, wherein the electrode layers are adapted for altering the optical power of the spectacle lens, and wherein each of the electrode layers has a conductivity associated therewith, wherein said conductivities associated with each of at least two of said electrode layers are different, one from the other, and wherein at least two of the modal liquid crystal cells have substantially different diameters; and
- a controller for directing application of voltage to each of the electrode layers.

13. The electro-active spectacle lens of claim 12, wherein at least two of the electrode layers are adapted to produce a retardance profile across one of the modal liquid crystal cells.

14. The electro-active spectacle lens of claim 12, wherein at least two of the electrode layers are adapted to produce spherical power across one of the modal liquid crystal cells.

15. The electro-active spectacle lens of claim 14, wherein at least two of the electrode layers are adapted to produce spherical power across a second one of the modal liquid crystal cells.

16. The electro-active spectacle lens of claim 12, further comprising at least two bus electrodes respectively coupled to at least two of the electrode layers.

17. The electro-active spectacle lens of claim 12, further comprising a spacer ring disposed between at least two of the plurality of modal liquid crystal cells.

18. The electro-active spectacle lens of claim 12, further comprising a base lens attached to one of the plurality of modal liquid crystal cells.

19. An electro-active spectacle lens comprising:
- a first modal liquid crystal lens assembly having a first electro-active cell with a first diameter, the first modal liquid crystal lens assembly comprising a first electrode layer with outer and inner electrode regions with the conductivity of the outer electrode region greater than the conductivity of the inner electrode region and a second electrode layer having a third conductivity and an electro-active material between the first and second electrode layers; and
- a second modal liquid crystal lens assembly attached to the first modal liquid crystal lens assembly, the second modal liquid crystal lens assembly having a second electro-active cell with a second diameter, the second modal liquid crystal lens assembly comprising a first electrode layer with outer and inner electrode regions with the conductivity of the outer electrode region greater than the conductivity of the inner electrode region and a second electrode layer having a third conductivity and an electro-active material between the first and second electrode layers; the second diameter being greater than the first diameter of the first electro-active cell.

20. The electro-active spectacle lens of claim 19, wherein the first electro-active cell and second electro-active cell are adapted to produce a first blended zone in the electro-active spectacle lens.

21. The electro-active spectacle lens of claim 1, further comprising a progressive addition lens.

22. The electro-active spectacle lens of claim 19, further comprising a progressive addition lens.

* * * * *